(12) United States Patent
Roselli

(10) Patent No.: US 9,808,363 B2
(45) Date of Patent: Nov. 7, 2017

(54) FRAME STRUCTURES, STENT GRAFTS INCORPORATING THE SAME, AND METHODS FOR EXTENDED AORTIC REPAIR

(71) Applicant: THE CLEVELAND CLINIC FOUNDATION, Cleveland, OH (US)

(72) Inventor: Eric E. Roselli, Rocky River, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 91 days.

(21) Appl. No.: 14/849,785

(22) Filed: Sep. 10, 2015

(65) Prior Publication Data

US 2016/0067067 A1 Mar. 10, 2016

Related U.S. Application Data

(60) Provisional application No. 62/048,327, filed on Sep. 10, 2014.

(51) Int. Cl.
*A61F 2/07* (2013.01)
*A61F 2/89* (2013.01)
(Continued)

(52) U.S. Cl.
CPC .................. *A61F 2/89* (2013.01); *A61F 2/07* (2013.01); *A61F 2/848* (2013.01); *A61F 2/856* (2013.01);
(Continued)

(58) Field of Classification Search
CPC .................. A61F 2/82; A61F 2/06; A61F 2/89
(Continued)

(56) References Cited

U.S. PATENT DOCUMENTS 6,835,203 B1 * 12/2004 Vardi .................. A61F 2/82
623/1.34
8,123,795 B1 2/2012 Knodel et al.
(Continued)

FOREIGN PATENT DOCUMENTS

| EP | 1208816 A2 | 5/2002 |
| EP | 1946725 A1 | 7/2008 |
| EP | 2066269 A2 | 6/2009 |

OTHER PUBLICATIONS

Akasaka, Junetsu, et al. "Stent grafting technique using Matsui-Kitamura (MK) stent for patients with aortic arch aneurysm." European journal of cardio-thoracic surgery 27.4 (2005): 649-653.
(Continued)

*Primary Examiner* — Suzette J Gherbi
(74) *Attorney, Agent, or Firm* — Tarolli, Sundheim, Covell & Tummino LLP

(57) ABSTRACT

One aspect of the present disclosure can include a frame structure adapted for use with a stent graft. The frame structure can include a scallop region and a Z-form region. The scallop region can have a first end portion, a second end portion, and a perimeter that defines an aperture. The Z-form region can extend from the scallop region and include a plurality of Z-shaped struts, each of which has a first end and a second end that is connected to the scallop region at different points so as to form a central frame structure lumen. The second end portion of the scallop region can include a backstop that is deployable from a first flattened configuration to a second erect configuration. The backstop, in the second erect configuration, is sized and dimensioned to extend into a lumen of an aortic branch vessel.

13 Claims, 11 Drawing Sheets

(51) Int. Cl.
  *A61F 2/848* (2013.01)
  *A61F 2/856* (2013.01)
  *A61F 2/91* (2013.01)
  *A61F 2/06* (2013.01)

(52) U.S. Cl.
  CPC .......... *A61F 2/91* (2013.01); *A61F 2002/061* (2013.01); *A61F 2002/075* (2013.01); *A61F 2220/0008* (2013.01); *A61F 2230/008* (2013.01); *A61F 2230/0045* (2013.01)

(58) Field of Classification Search
  USPC ................................................ 623/1.15–1.48
  See application file for complete search history.

(56) References Cited

U.S. PATENT DOCUMENTS

| | | | | |
|---|---|---|---|---|
| 8,298,278 | B2* | 10/2012 | Gregorich | A61F 2/856 623/1.1 |
| 8,298,280 | B2* | 10/2012 | Yadin | A61F 2/856 623/1.15 |
| 8,932,340 | B2* | 1/2015 | Meyer | A61F 2/856 623/1.11 |
| 9,114,033 | B2* | 8/2015 | Feld | A61F 2/856 |
| 9,211,183 | B2* | 12/2015 | Ivancev | A61F 2/07 |
| 9,427,340 | B2* | 8/2016 | Yadin | A61F 2/856 |
| 2003/0088305 | A1* | 5/2003 | Van Schie | A61F 2/06 623/1.12 |
| 2006/0173528 | A1 | 8/2006 | Feld et al. | |
| 2007/0260304 | A1 | 11/2007 | Gregorich et al. | |
| 2008/0177377 | A1 | 7/2008 | Meyer et al. | |
| 2009/0030502 | A1* | 1/2009 | Sun | A61F 2/07 623/1.16 |
| 2009/0163994 | A1 | 6/2009 | Quigley et al. | |
| 2009/0240318 | A1* | 9/2009 | Chalekian | A61F 2/856 623/1.16 |
| 2009/0287145 | A1 | 11/2009 | Cragg et al. | |
| 2010/0057186 | A1* | 3/2010 | West | A61F 2/064 623/1.13 |
| 2010/0131041 | A1 | 5/2010 | Lewis et al. | |
| 2010/0268327 | A1* | 10/2010 | Bruszewski | A61F 2/07 623/1.18 |
| 2011/0153002 | A1* | 6/2011 | Davidson | A61F 2/82 623/1.16 |
| 2012/0221090 | A1* | 8/2012 | Wolf | A61F 2/07 623/1.11 |
| 2013/0079870 | A1* | 3/2013 | Roeder | A61F 2/07 623/1.35 |
| 2013/0138203 | A1* | 5/2013 | Quadri | A61F 2/2418 623/1.16 |
| 2013/0345785 | A1* | 12/2013 | Hartley | A61F 2/07 623/1.2 |
| 2014/0180393 | A1* | 6/2014 | Roeder | A61F 2/06 623/1.15 |
| 2014/0243952 | A1* | 8/2014 | Parodi | A61F 2/07 623/1.35 |
| 2014/0316513 | A1* | 10/2014 | Tang | A61F 2/2412 623/1.16 |
| 2015/0164642 | A1* | 6/2015 | Khosravi | A61F 2/915 623/1.25 |
| 2015/0173920 | A1* | 6/2015 | Bruszewski | A61F 2/07 623/1.35 |
| 2016/0030209 | A1* | 2/2016 | Shalev | A61F 2/07 623/1.35 |
| 2016/0184115 | A1* | 6/2016 | Ondersma | A61F 2/856 623/1.35 |
| 2016/0346042 | A1* | 12/2016 | Nomiyama | G06T 17/00 |
| 2017/0007391 | A1* | 1/2017 | Inoue | A61F 2/89 |
| 2017/0056152 | A1* | 3/2017 | Kelly | A61F 2/07 |

OTHER PUBLICATIONS

Criado, Frank J., et al. "Early Experience with the Talent™ Stent-Graft System for Endoluminal Repair of Abdominal Aortic Aneurysms." Texas Heart Institute Journal 27.2 (2000): 128.

Czerny, Martin, et al. "Initial results after combined repair of aortic arch aneurysms by sequential transposition of the supra-aortic branches and consecutive endovascular stent-graft placement." The Annals of thoracic surgery 78.4 (2004): 1256-1260.

Inglese, Luigi, et al. "Endovascular repair of thoracic aortic disease with the EndoFit stent-graft: short and midterm results from a single center." Journal of Endovascular Therapy 15.1 (2008): 54-61.

Ishimaru, Shin. "Endografting of the aortic arch." Journal of Endovascular Therapy 11.SupplementII (2004): II-62.

Kutty, Shelby, et al. "Endovascular stent grafts for large thoracic aneurysms after coarctation repair." The Annals of thoracic surgery 85.4 (2008): 1332-1338.

Lima, Brian, et al. "Modified and "reverse" frozen elephant trunk repairs for extensive disease and complications after stent grafting." The Annals of thoracic surgery 93.1 (2012): 103-109.

Mertens, Renato, et al. "Ventana fenestrated stent-graft system for endovascular repair of juxtarenal aortic aneurysms." Journal of Endovascular Therapy 19.2 (2012): 173-178.

Roselli, Eric E., et al. "Antegrade delivery of stent grafts to treat complex thoracic aortic disease." The Annals of thoracic surgery 90.2 (2010): 539-546.

Roselli, Eric E., et al. "Simplified frozen elephant trunk repair for acute DeBakey type I dissection." The Journal of thoracic and cardiovascular surgery 145.3 (2013): S197-S201.

PCT Invitation to Pay Additional Fees for PCT/US2015/049301, mailed Nov. 9, 2015, pp. 1-5.

* cited by examiner

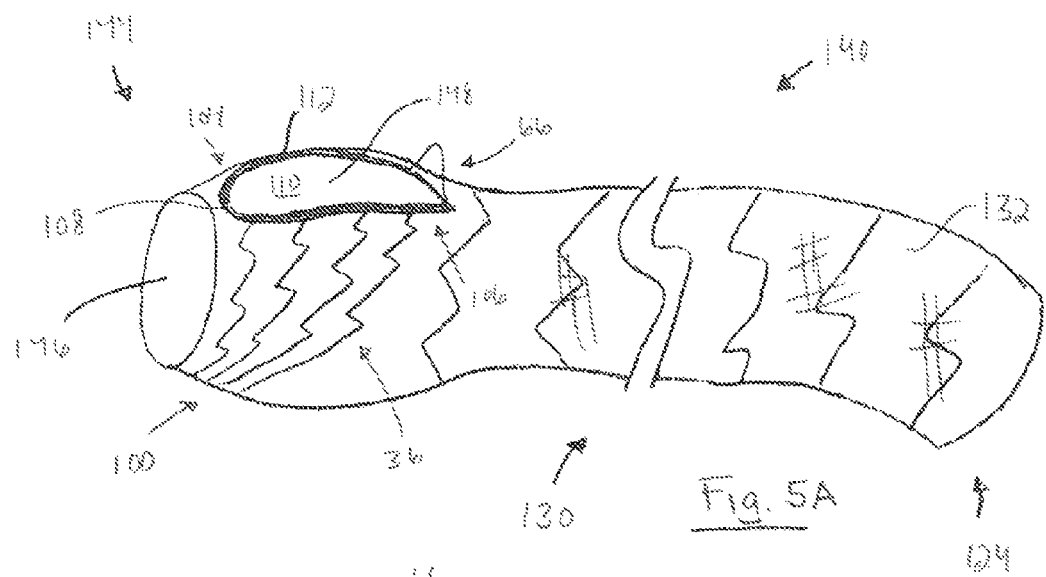

FRAME STRUCTURES, STENT GRAFTS INCORPORATING THE SAME, AND METHODS FOR EXTENDED AORTIC REPAIR

RELATED APPLICATION

This application claims the benefit of U.S. Provisional Patent Application No. 62/048,327, filed Sep. 10, 2014, the entirety of which is hereby incorporated by reference for all purposes.

TECHNICAL FIELD

The present disclosure relates generally to vascular repair of bodily vessels, and more particularly to frame structures, stent grafts incorporating the frame structures, and related methods for repairing aortic abnormalities.

BACKGROUND

A leading cause of disability and death in both the U.S. and abroad includes damage to a portion of the vascular system. This is a particular problem with regard to aortic aneurysms. Diseases of the aorta, for example, are becoming an increasing concern as a result of advancements in cardiac surgery and human longevity. Severe arterial sclerosis, severely calcified aorta, and other indications continue to necessitate complete or partial aortic replacement procedures.

Aneurysms are typically characterized by diseased or damaged blood vessels which lead to a weakening of the vessel wall. Weakening of the vessel wall can then lead to a blood-filled dilation of the vessel. Left untreated, aneurysms will eventually rupture and result in acute (and often fatal) hemorrhaging in a very short period of time.

The aorta has numerous arterial branches. The arch of the thoracic aorta, for example, has three major branches arising from the convex upper surface of the arch and ascending through the superior thoracic aperture to the root of the neck. The proximity of an aneurysm to a branch artery may limit the use of an excluding device, such as a tubular stent graft. For example, the main body or ends of a tubular stent graft may occlude or block the branch arteries as a result of positioning the stent graft against a healthy, i.e., non-diseased or dilated portion of the artery wall. Additionally, there may be an inadequate length of healthy tissue for the stent graft to seal against in the area between the aneurysm and the location of the branch arteries. Even if the stent graft is initially located without blocking a branch artery, there still is a risk that the devices will migrate to a position where it may partially or fully block a branch artery.

SUMMARY

One aspect of the present disclosure can include a frame structure adapted for use with a stent graft. The frame structure can include a scallop region and a Z-form region. The scallop region can have a first end portion, a second end portion, and a perimeter that defines an aperture. The Z-form region can extend from the scallop region and include a plurality of Z-shaped struts, each of which has a first end and a second end that is connected to the scallop region at different points so as to form a central frame structure lumen. The second end portion of the scallop region can include a backstop that is deployable from a first flattened configuration to a second erect configuration. The backstop, in the second erect configuration, is sized and dimensioned to extend into a lumen of an aortic branch vessel.

Another aspect of the present disclosure can include a stent graft that is movable between a collapsed configuration and an expanded configuration. The stent graft can comprise an elongated body having a proximal end portion, a distal end portion, an intermediate portion extending between the proximal and distal end portions, and a lumen extending between the proximal and distal end portions. The proximal end portion can include a frame structure, and the intermediate and distal end portions can include an expandable support member. Each of the frame structure and the expandable support member can have at least one surface thereof covered by a biocompatible graft material. The proximal end portion can include an aperture that is in fluid communication with the lumen, and is defined by a portion of the frame structure. The frame structure can include a deployable backstop configured to extend into a lumen of an aortic arch branch vessel when the stent graft is implanted in a subject.

Another aspect of the present disclosure can include a method for repairing at least a portion of a diseased aortic arch in a subject. One step of the method can include providing a stent graft. The stent graft can include an elongated body having a proximal end portion, a distal end portion, an intermediate portion extending between the proximal and distal end portions, and a lumen extending between the proximal and distal end portions. The proximal end portion can include a frame structure, and the intermediate and distal end portions can include an expandable support member. Each of the frame structure and the expandable support member can have at least one surface thereof covered by a biocompatible graft material. The proximal end portion can include an aperture that is in fluid communication with the lumen and defined by a portion of the frame structure. The main body can be positioned in the diseased portion of the aortic arch so that the frame structure is located immediately adjacent the aortic arch branch vessels. Next, the backstop can be deployed from a first flattened configuration into a second erect configuration whereby the backstop extends into a lumen of one of the aortic arch branch vessels. The main body can then be securely implanted in the subject. The backstop, when located in the lumen of the aortic arch branch vessel, prevents migration of the stent graft and provides a seal with the aortic arch branch vessel.

BRIEF DESCRIPTION OF THE DRAWINGS

The foregoing and other features of the present disclosure will become apparent to those skilled in the art to which the present disclosure relates upon reading the following description with reference to the accompanying drawings, in which:

FIG. 5A is a perspective view of an expandable support member comprising a stent graft according to another aspect of the present disclosure;

FIG. 5B is a view taken from a proximal end portion of the expandable support member in FIG. 5A;

FIG. 5C is a top view of the expandable support member in FIG. 5A;

DETAILED DESCRIPTION

Definitions

Figure 1A:
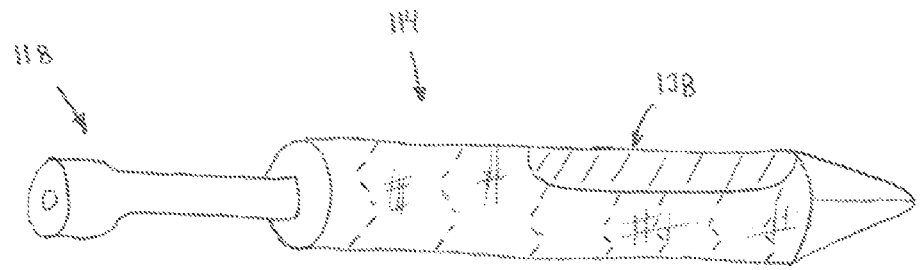
FIGS. 1A-B are schematic illustrations showing perspective views showing a stent graft in a collapsed configuration (FIG. 1A) and an expanded configuration (FIG. 1B) according to one aspect of the present disclosure.

Unless otherwise defined, all technical terms used herein have the same meaning as commonly understood by one of ordinary skill in the art to which the present disclosure pertains.

In the context of the present disclosure, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of the apparatus in use or operation in addition to the orientation depicted in the figures. For example, if the apparatus in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

As used herein, the term "subject" can be used interchangeably with the term "patient" and refer to any warm-blooded organism including, but not limited to, human beings, pigs, rats, mice, dogs, goats, sheep, horses, monkeys, apes, rabbits, cattle, etc.

As used herein, the term "stent graft" can generally refer to a prosthesis comprising an expandable support member (e.g., a stent) and a graft material associated therewith that forms a lumen through at least a portion of its length.

As used herein, the term "biocompatible" can refer to a material that is substantially non-toxic in the in vivo environment of its intended use, and that is not substantially rejected by a patient's physiological system (i.e., is non-antigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity and/or immunogenicity. A biocompatible structure or material, when introduced into a majority of patients, will not cause a significantly adverse, long-lived or escalating biological reaction or response, and is distinguished from a mild, transient inflammation which typically accompanies surgery or implantation of foreign objects into a living organism.

As used herein, the term "endoleak" can refer to the presence of blood flow past the seal between the end of a stent graft and the vessel wall (Type I), and into the aneurysmal sac, when all such flow should be contained within the stent graft's lumen.

As used herein, the term "migration" can refer to displacement of a stent graft from its intended implantation site.

As used herein, the terms "placed stent graft" or "implanted stent graft" can refer to a surgically placed or implanted stent graft, either by invasive or non-invasive techniques.

Overview

Figure 1B:
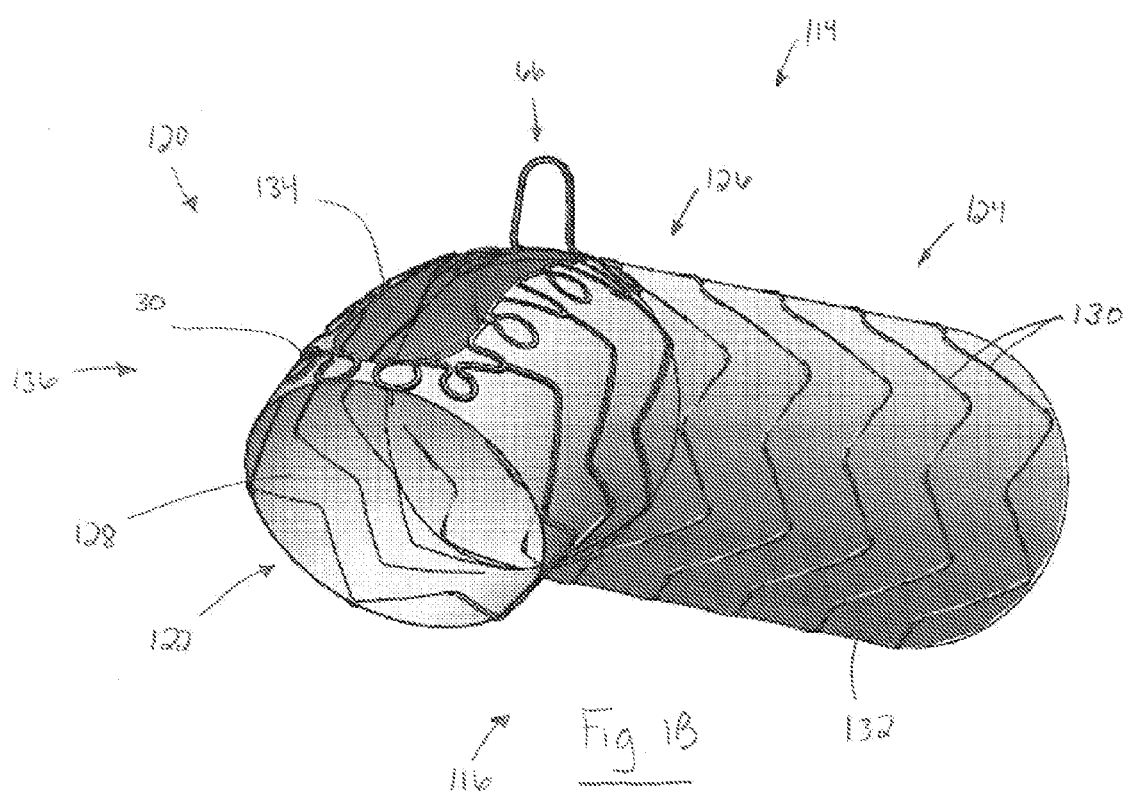

The present disclosure relates generally to vascular repair of bodily vessels, and more particularly to a stent graft and related method for repairing aortic abnormalities. As representative of one aspect of the present disclosure, FIGS. 1A-B illustrate a stent graft 10 to facilitate extended repair in patients with vascular abnormalities, such as aortic disease (e.g., aortic dissection or aneurysm). There is currently growing interest in performing extended aortic repair at the time of acute aortic dissection. No devices for doing so are currently available in the U.S., and the device available in Europe requires a complex operation to deploy it. As described in more detail below, aspects of the present disclosure allow for the extended repair technique (also known as the frozen elephant trunk technique) to be more widely adapted, while also permitting better repair of the aorta during an emergency procedure. It will be appreciated that aspects of the present disclosure may also be used to treat vascular trauma, arteriosclerosis, calcification, microbial infection, congenital defects, and other obstructive diseases associated with the aorta.

Figure 2:
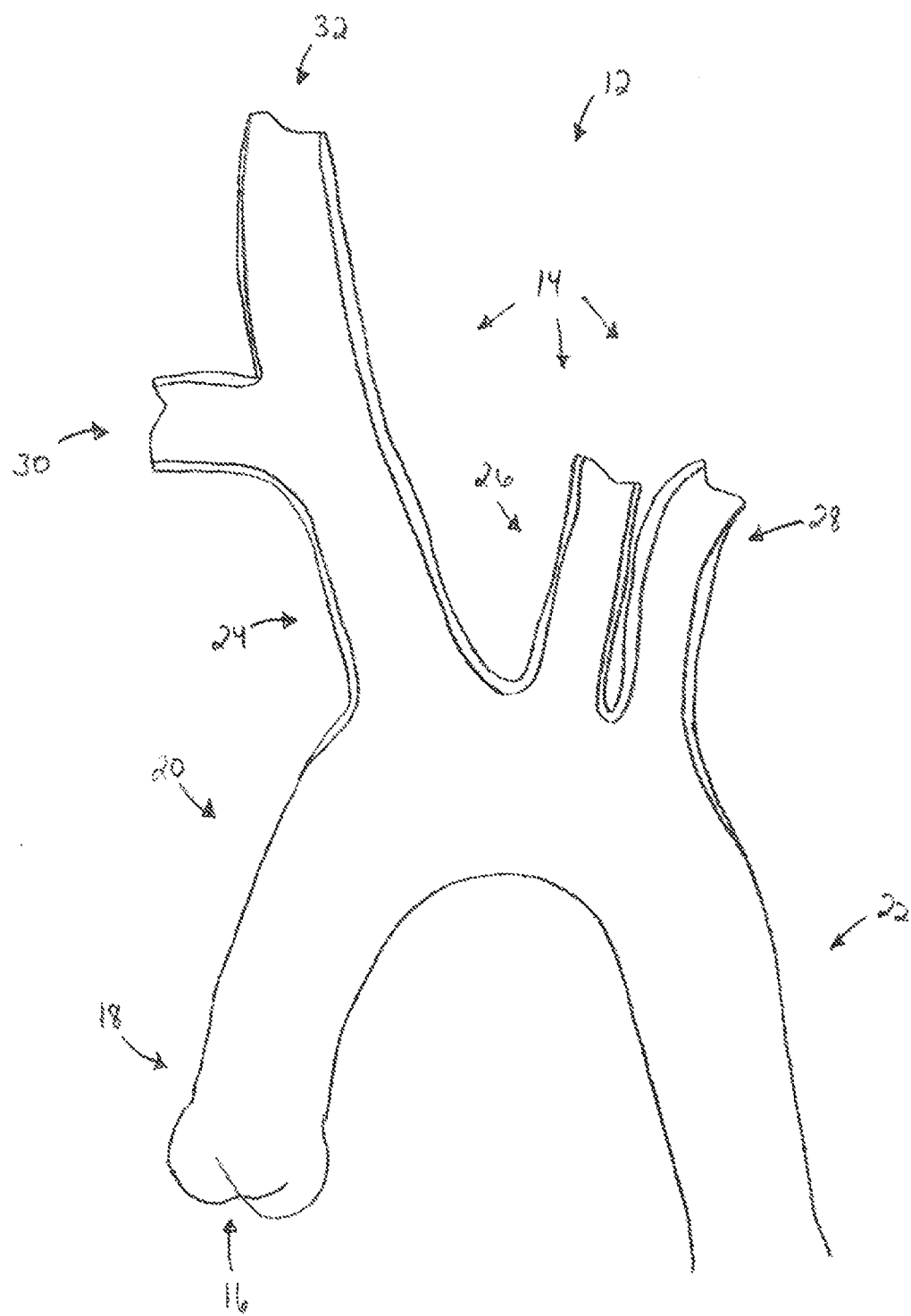
FIG. 2 is a cross-sectional view of an aortic arch.

To assist the reader in understanding the relevant anatomy and physiology to which certain aspects of the present disclosure pertain, FIG. 2 illustrates a cross-sectional view of a human aortic arch 12, including the aortic arch branch vessels 14. The aorta is the largest vessel in the body. It transports oxygenated blood from the left ventricle of the heart (not shown) to every organ. The aorta starts in the heart with the aortic valve 16, which is immediately adjacent the aortic root 18 and followed by the ascending aorta 20, the transverse aorta 12 or aortic arch, the descending aorta 22, and the thoracoabdominal aorta (not shown). The aorta ends in the abdomen after bifurcation of the abdominal aorta in the two common iliac arteries (not shown). The aortic arch 12 gives off the brachiocephalic trunk 24, the left common carotid artery 26, and the left subclavian artery 28. The brachiocephalic trunk 24 splits to form the right subclavian and the right common carotid arteries 30 and 32, which supply blood to the right arm and the right side of the neck and head. The left common carotid artery 26 and left subclavian artery 28 perform parallel functions on the left side.

Frame Structures

One aspect the present disclosure can include frame structures adapted for use with a stent graft. The frame structures can be self-expanding, stent-like structures configured to transition from a collapsed configuration (e.g., during delivery) to an expanded configuration (e.g., upon implantation). The frame structures can be made from one or a combination of elastic or superelastic materials, such as Nitinol, Cobalt Chromium, and 316L Stainless steel. In some instances, the frame structures can be formed using one or more lasercutting steps (e.g., using a thermal femto-second laser to cut an appropriately-sized Nitinol sheet). The cut frame structure can then be applied to a shape-setting mandrel and treated (e.g., heated to about 350° C., baked for about 10 minutes, and then quenched in room temperature water) to obtain a desired configuration. The frame structures can be formed from a single, unitary wire or from two or more wires.

Examples of frame structures are illustrated below. Generally speaking, the frame structures can include a scallop region and a Z-form region extending therefrom. The scallop region can have a first end portion, a second end portion, and a perimeter that defines an aperture. The Z-form region can extend from the scallop region and comprise a plurality of Z-shaped struts. Each of the Z-shaped struts has a first end and a second end that extends from, or is connected to, the scallop region at a different point so as to form a central frame structure lumen. The second end portion of the scallop region includes a backstop that is deployable from a first flattened configuration to a second erect configuration. In the second erect configuration, the backstop can be sized and dimensioned to extend into a lumen of an aortic branch vessel. In one example, the backstop 36 can have a width of about 3 mm to about 15 mm or more (e.g., about 6 mm to about 9 mm, such as 8 mm) and a height of about 2 mm to about 3 cm or more (e.g., about 10 mm). Advantageously, the ability of the backstop to extend into the lumen of an aortic arch branch vessel 14 prevents migration of a stent graft associated with the frame structure once implanted. Additionally, the backstop advantageously optimizes the seal formed between an associated stent graft and the aortic arch branch vessel 14 (that receives the backstop), which may be vulnerable to endoleaks and where tears in complex dissections often occur.

Figure 3A:
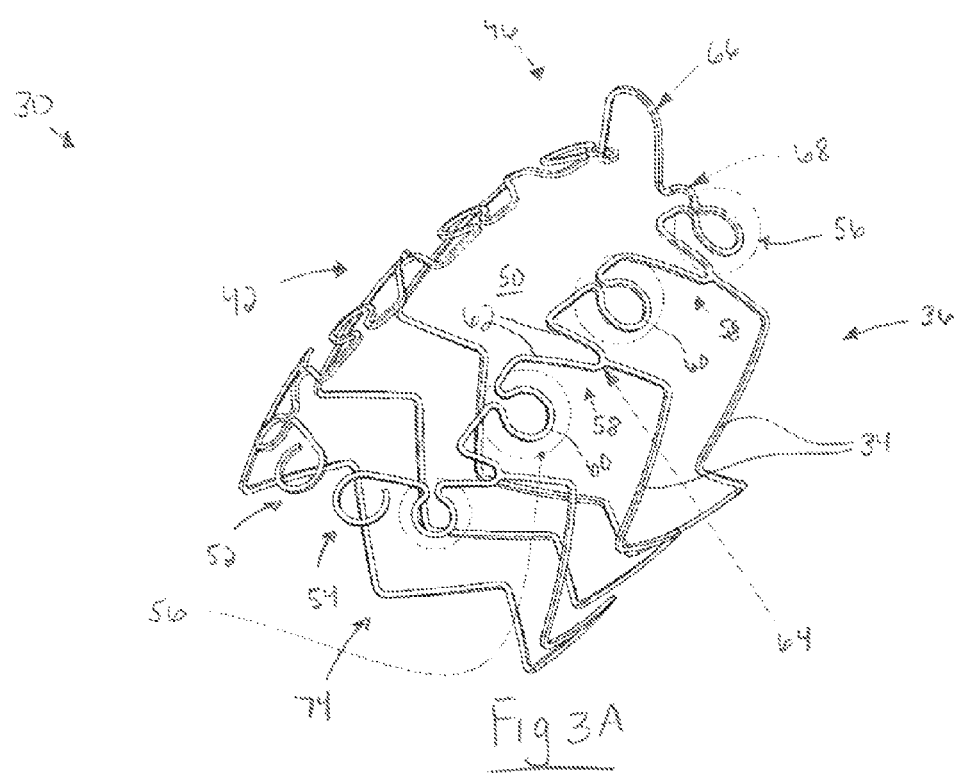
FIG. 3A is a schematic illustration showing a perspective view of a frame structure comprising the stent graft in FIG. 1B.
Figure 3B:
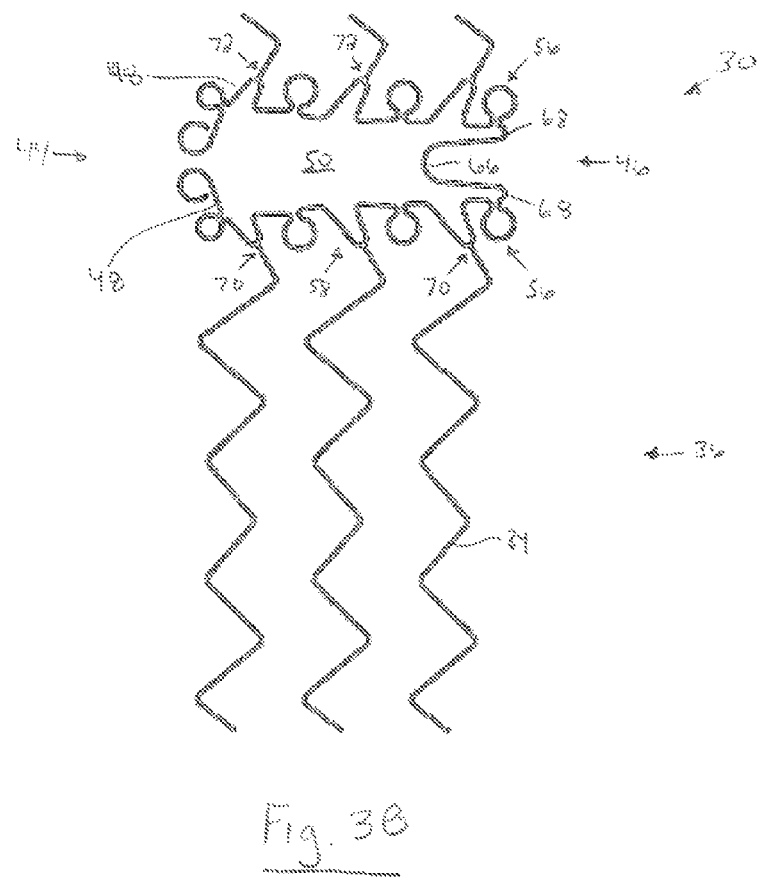
FIG. 3B is a schematic illustration showing a top view of the frame structure in FIG. 3A in a disassembled configuration.
Figure 3C:
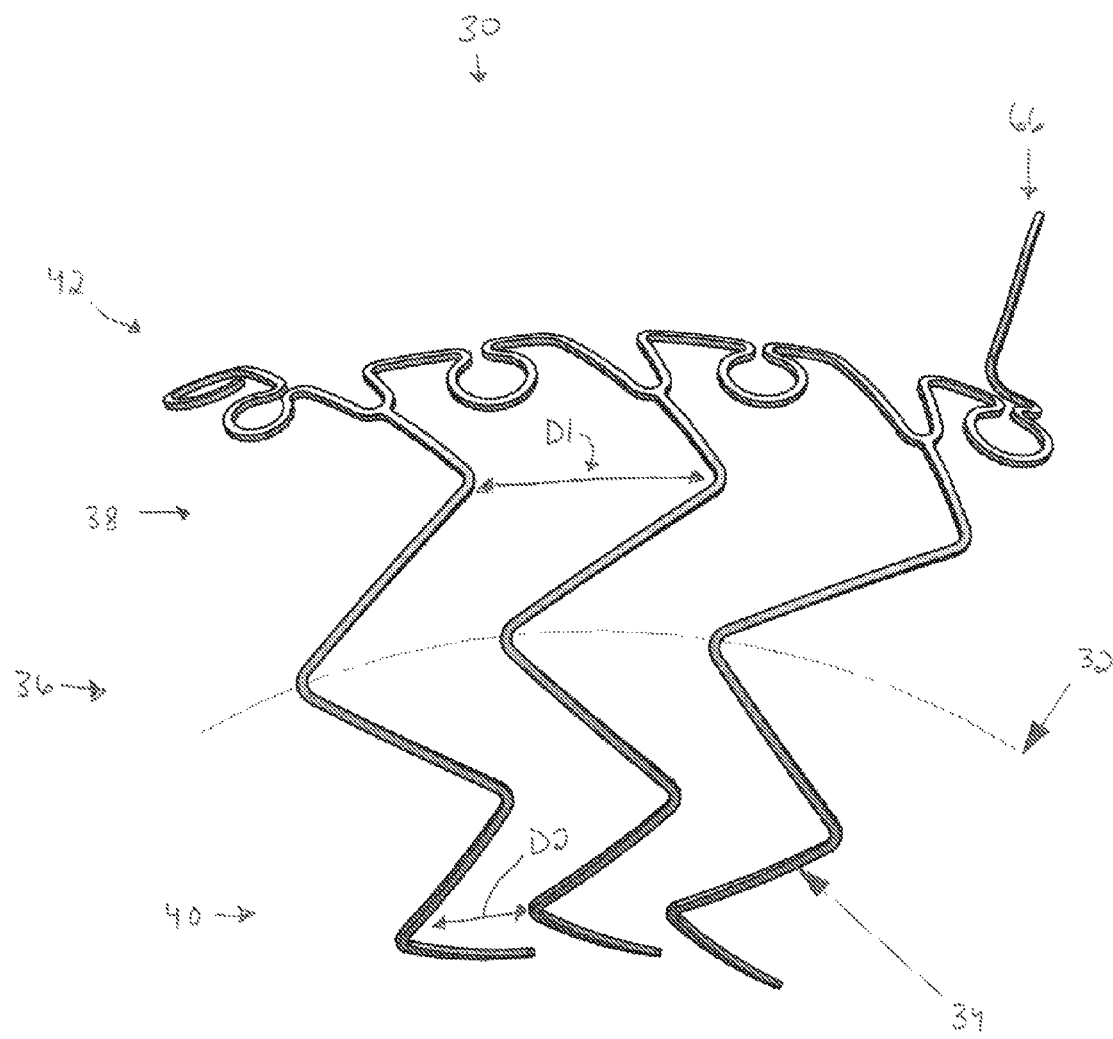
FIG. 3C is a schematic illustration showing a side view of the frame structure in FIGS. 3A-B.

One example of a frame structure 30 for use with a stent graft is illustrated in FIGS. 3A-C. The frame structure 30 can have an arch-shaped centerline 32 (FIG. 3C) that mirrors the arch-shaped centerline of an aortic arch 12. In other words, the centerline 32 of the frame structure 30 has an arcuate shape (e.g., a radius of curvature that is equal or about equal to the radius of curvature of the aortic arch 12). The arch-shaped centerline 32 advantageously allows the frame structure 30 (and a stent graft associated therewith) to conform to the aortic arch 12 and ensure proper sealing, once implanted, to avoid endoleaks. The arch-shaped centerline 32 is achieved, at least in part, by the spacing associated with Z-shaped struts 34 that form a Z-region 36 of the frame structure 30. As shown in FIG. 3C, for example, the distance D1 between the struts 34 at an upper portion 38 of the Z-form region 36 is greater than the distance D2 between the same struts at a lower portion 40 of the Z-form region. The difference between D1 and D2 creates a taper from the upper portion 38 to the lower portion 40 that, in turn, results in the arch-shaped centerline 32.

Referring to FIGS. 3A-B, the frame structure 30 can comprise a scallop region 42 and a Z-form region 38 extending therefrom. As discussed below, the profile of the scallop region 41 advantageously allows for a balance of strength and stretch in the region around the ascending vessels of the aortic arch 12. The scallop region 42 can have a first end portion 44, a second end portion 46, and a perimeter 48 that defines an aperture 50. The aperture 50 is sized and dimensioned to surround the origins of each of the supra-aortic vessels. In some instances, the aperture 50 can have a length of about 20-50 mm (e.g., 42 mm) and a width of about 9-20 mm (e.g., 14-15 mm). The scallop region 42 can be formed from a single wire or from two or more wires. The wire(s) forming the scallop region 42 can form a continuous or discontinuous ring. As shown in FIGS. 3A-B, for example, a single wire forming the scallop region 42 can form a discontinuous ring such that first and second free ends 52 and 54 are located at the first end portion 44. In this case, the first and second free ends 52 and 54 terminate as loop-shaped structures that facilitate attachment of the frame structure 30 to a graft material.

The scallop region 42 can comprise a plurality of attachment members 56 that are spaced apart from one another by one or more peak-shaped structures 58. In one example, one or more (e.g., all) of the attachment members 56 can be omega-shaped and include an arcuate segment 60 that is free from direct attachment to any of the Z-shaped struts 34. By "free from direct attachment to any of the Z-shaped struts 34", it is meant that at last one intervening structure (e.g., a peak-shaped structure 58) is located between the arcuate segment 60 of the attachment member 56 and a Z-shaped strut 34. Advantageously, attachment members 56 having an omega-shaped configuration permit a high degree of stretch as a result of having a longer length over which to spread out the force (essentially a softer spring constant). In one example, the scallop region 42 can include eight omega-shaped attachment members 56. The attachment members 56 can facilitate attachment of the frame structure 30 to a graft material (e.g., by receiving one or more fasteners, such as sutures and/or ETV clips) therethrough. The attachment members 56 can be evenly or unevenly spaced apart from one another or from the peak-shaped structures 58.

The peak-shaped structures 58 comprising the scallop region 42 can have a V-shaped, U-shaped, or arch-shaped configuration. The peak-shaped structures 58 comprising the scallop region 42 can have the same or different configuration, such as those just mentioned. Each peak-shaped structure 58 can be comprised of two straight segments 62 that converge at an apex 64. A Z-shaped strut 34 can extend from, or be directly connected to, an apex 64 of each peak-shaped structure 58. In one example, the scallop region 42 can include six peak-shaped structures 58. Advantageously, the transition of the scallop region 42 into the Z-form region 36 at the peak-shaped structures 58 facilitates compression of the frame structure 30 (and associated stent graft) into a delivery catheter, as with a conventional stent graft.

Figure 6A:
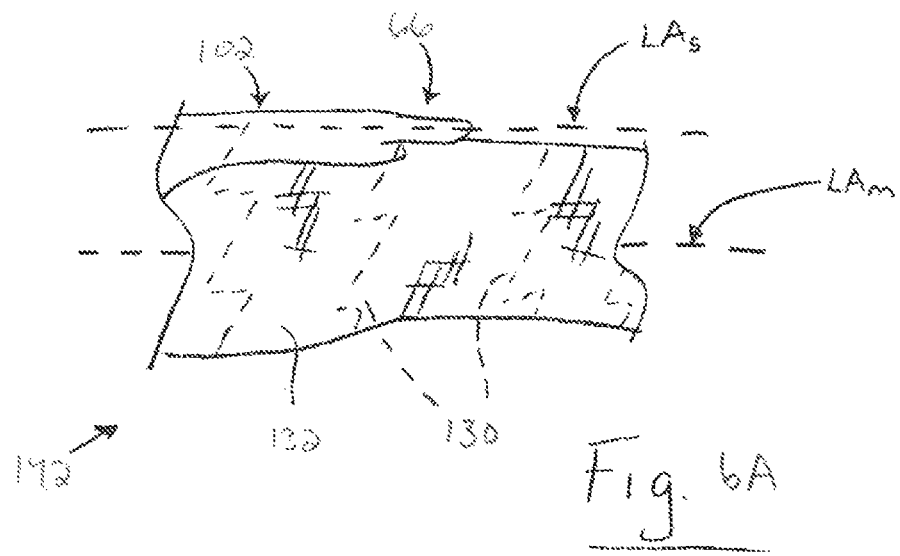
FIGS. 6A-B are perspective views showing transition of a backstop comprising the stent graft in FIGS. 5A-C from a flattened configuration (FIG. 6A) to an erect configuration (FIG. 6B)
Figure 6B:
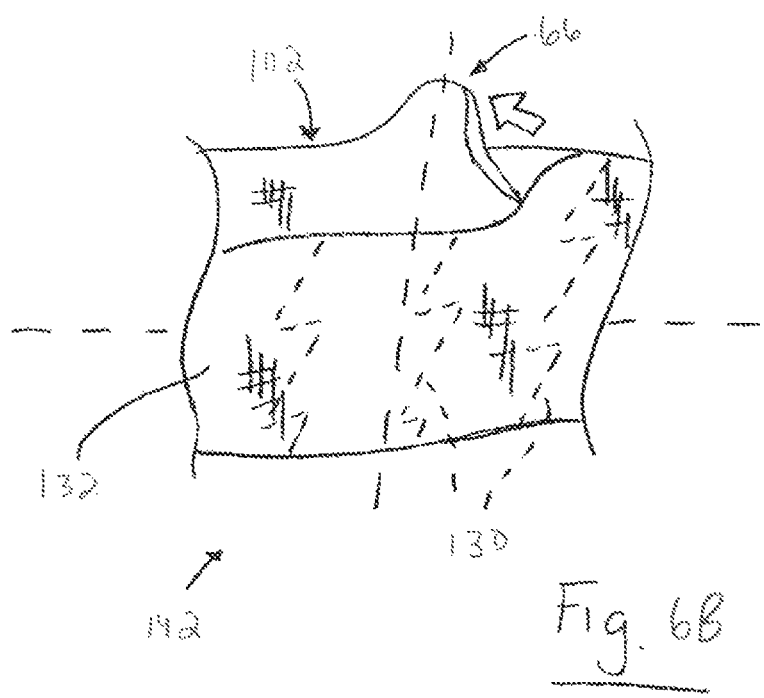
Figure 7:
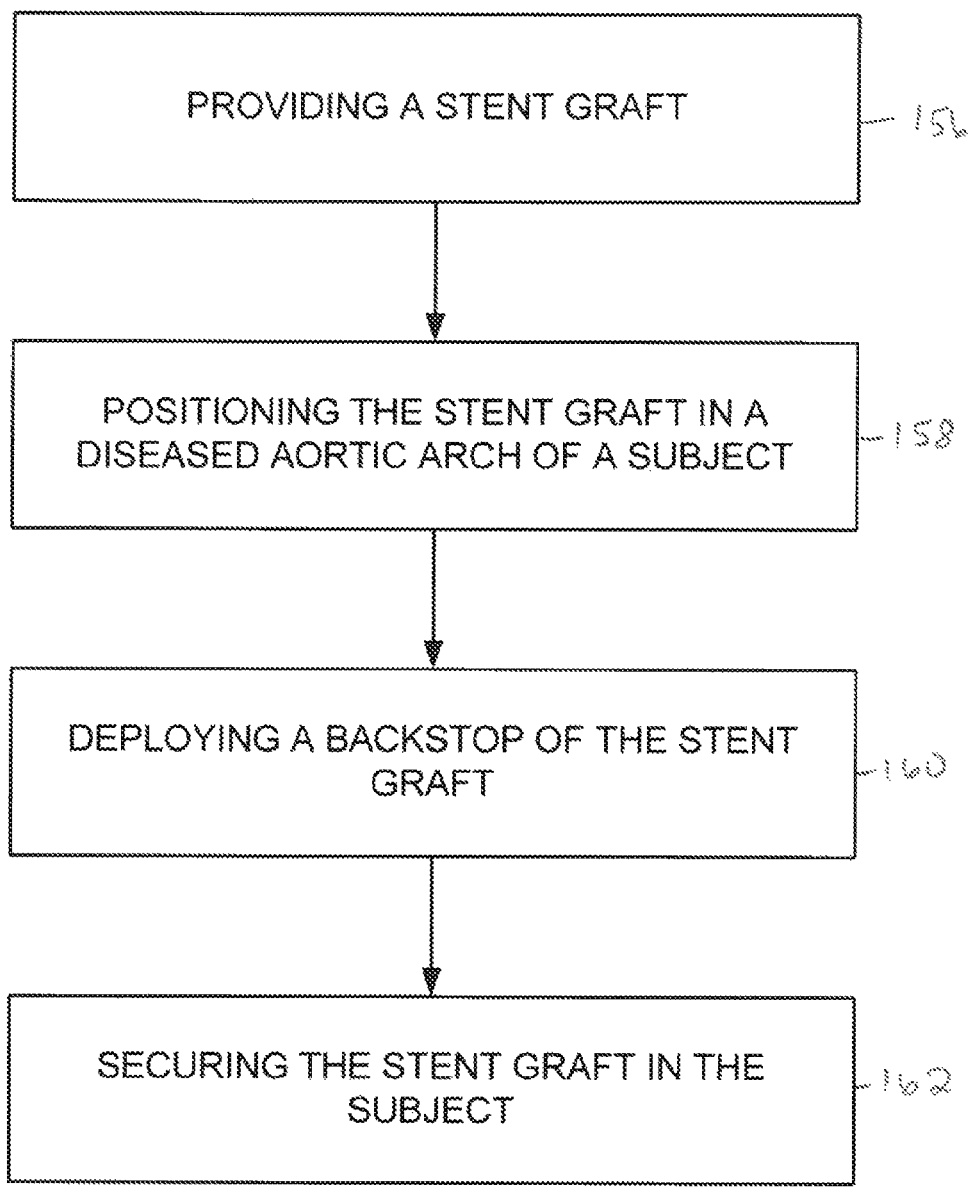
FIG. 7 is a process flow diagram illustrating a method for repairing at least a portion of a diseased aortic arch according to another aspect of the present disclosure.

The second end portion 46 of the scallop region 42 can include a backstop 66. The backstop 66 can be comprised of the same or different wire(s) as the wire(s) comprising the rest of the scallop region 42. The backstop 66 is deployable from a first flattened configuration (FIG. 3B) to a second erect configuration (FIGS. 3A and 3C), one example of which is illustrated in FIGS. 6A-B. Methods for deploying the backstop 66 are discussed below. Generally, however, the backstop 66 can be deployed automatically (e.g., by "popping up" upon removal of a constraining material thereon) or manually (e.g., by actuation of a pullwire or other similar mechanism). In the flattened configuration, the backstop 66 can extend in a coaxial or substantially coaxial manner relative to the centerline 32 of the frame structure 30. In the erect configuration, the backstop 66 can extend radially away from the scallop region 42. In the second erect configuration, the backstop 66 can be sized and dimensioned to extend into a lumen of an aortic branch vessel (e.g., the left subclavian artery 28). Advantageously, the backstop 66, when deployed in the second erect configuration, improves anchoring and sealing of a stent graft associated therewith.

The second end portion 46 of the scallop region 42 can further include at least one extension segment 68 that connects, and extends between, the backstop 66 and an attachment member 56. The extension segment 68 comprises an additional length that allows for a longer flexing area, thereby reducing strain and allowing use of a superelastic material (e.g., Nitinol) without any plastic deformation. As shown in FIG. 3A, the second end portion 46 of the scallop region 42 can include first and second extension segments 68, each of which has an arcuate configuration and extends between the backstop 66 and a respective attachment member 56.

The Z-form region 36 can extend from, or be directly connected to, the scallop region 42. The Z-form region 36 can comprise a plurality of Z-shaped struts 34. Advantageously, the use of Z-shaped struts 34 to form the Z-form region 36 allows for a balance of radial strength and compressibility of the frame structure 30. Each of the Z-shaped struts 34 has a first end 70 and a second end 72 (FIG. 3B). The first and second ends 70 and 72 can extend from, or be connected to, different points of the scallop region 42 so as to form a central frame structure lumen 74. For example, a first end 70 of a Z-shaped strut 34 can be connected to, or extend from, a first peak-shaped structure 58, and a second end 72 of the same Z-shaped strut can be connected to, or extend from, a second different peak-shaped structure of the scallop region 42. In one example, the Z-form region 36 can be comprised of three Z-shaped struts 34. It will be appreciated that the thickness, number, and spacing between the Z-shaped struts 34 comprising the Z-form region 36 can be adjusted as needed.

In one example of the present disclosure, the frame structure 30 can be comprised of one or more Nitinol wires and include eight omega-shaped attachment members 56, six peak-shaped structures 58, and three Z-shaped struts 34.

Figure 4A:
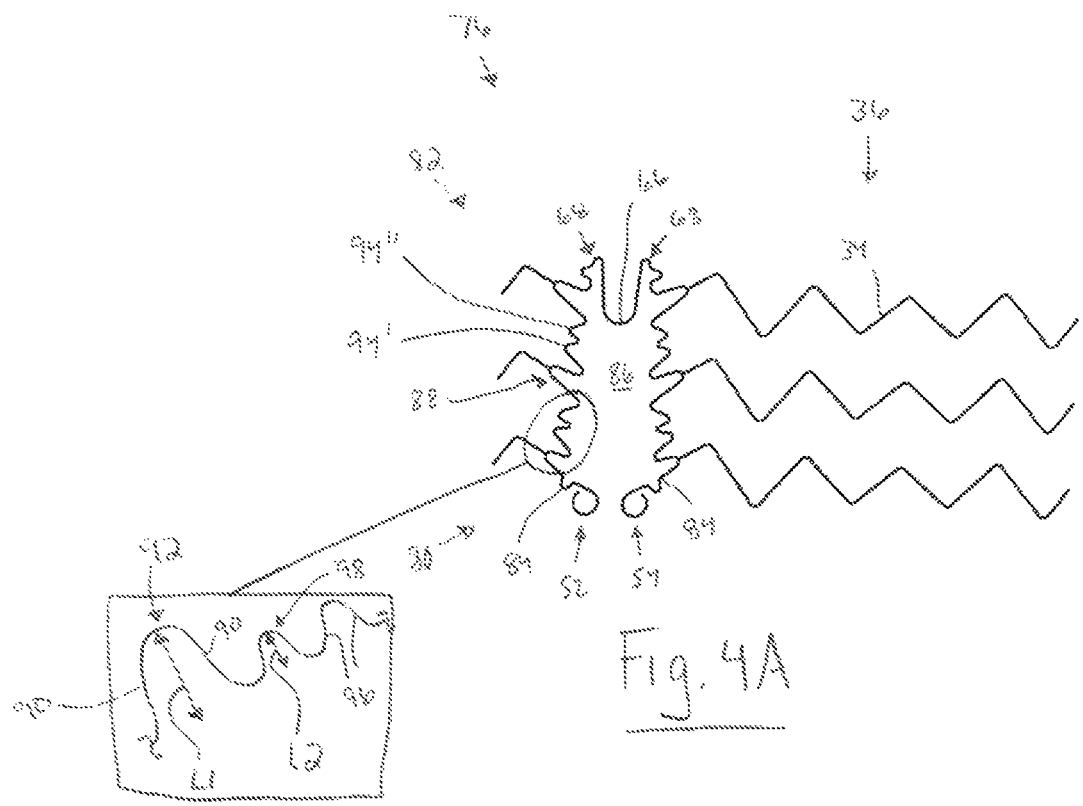
FIGS. 4A-B are schematic illustrations showing an alternative configuration of the frame structure in FIGS. 3A-C.
Figure 4B:

An alternative configuration of a frame structure 76 is shown in FIGS. 4A-B. The frame structure 76 can be identically constructed as the frame structure 30 shown in FIGS. 3A-B, except where described below. Thus, structures with the same reference numbers in FIGS. 4A-B are identical to the structures with the same reference number in FIGS. 3A-B, whereas different structures use different reference numbers. The frame structure 76 (FIGS. 4A-B) can comprise a scallop region 78 and a Z-form region 36 connected to or extending therefrom. The scallop region 78 can have a first end portion 80, a second end portion 82, and a perimeter 84 that defines an aperture 86. The Z-form region 36 can extend from the scallop region 78 and comprise a plurality of Z-shaped struts 34. Each of the Z-shaped struts 34 has a first end 70 and a second end 72 that extends from, or is connected to, the scallop region 78 at a different point so as to form a central frame structure lumen 74. The second end portion 82 of the scallop region 78 includes a backstop 66 that is deployable from a first flattened configuration to a second erect configuration. In the second erect configuration, the backstop 66 can be sized and dimensioned to extend into a lumen of an aortic branch vessel.

Unlike the scallop region 42 in FIGS. 3A-B, attachment members 88 comprising the scallop region 78 can be peak-shaped (e.g., V-shaped, U-shaped, or arch-shaped). Each attachment member 78 can be comprised of two straight segments 90 that converge at an apex 92. Each attachment member 88 can have a length L1 that extends from a base to the apex 92. A Z-shaped strut 34 can extend from, or be directly connected to, the apex 92 of each attachment member 88. In one example, the scallop region 78 can include six peak-shaped attachment members 88.

Each of the peak-shaped attachment members 88 can be spaced apart from one another by first and second peak-shaped structures 94' and 94". Each of the peak-shaped structures 94' and 94" can be V-shaped, U-shaped, or arch-shaped. Each of the peak-shaped structures 94' and 94" can be comprised of two straight segments 96 that converge at an apex 98. Each of the peak-shaped structures 94' and 94" can have a length L2 that extends from a base to an apex thereof 98. In some instances, the length L2 of each peak-shaped structure 94' and 94" is the same. In other instances, the length L2 of at least one peak-shaped structure 94' is different than the length L2 of one or more of the other peak-shaped structures 94". As shown in the exploded window of FIG. 4A, the length L1 of the attachment member 88 can be greater than the length L2 of each of the first and second peak-shaped structures 94' and 94".

An alternative configuration of a frame structure 100 is shown in FIGS. 5A-6B. The frame structure 100 can be identically constructed as the frame structures 30 and 76 shown in FIGS. 3A-B and FIGS. 4A-B, respectively, except where described below. Thus, structures with the same reference numbers in FIGS. 3A-B and FIGS. 4A-B are identical to the structures with the same reference number in FIGS. 5A-6B, whereas different structures use different reference numbers. The frame structure 100 (FIGS. 5A-6B)

can comprise a scallop region 102 and a Z-form region 36 extending therefrom. The scallop region 102 can have a first end portion 104, a second end portion 106, and a perimeter 108 that defines an aperture 110. The Z-form region 36 can extend from the scallop region 102 and comprise a plurality of Z-shaped struts 34. Each of the Z-shaped struts 34 has a first end 70 and a second end 72 that extends from, or is connected to, the scallop region 102 at a different point so as to form a central frame structure lumen 74. The second end portion 106 of the scallop region 102 includes a backstop 66 that is deployable from a first flattened configuration to a second erect configuration. In the second erect configuration, the backstop 66 can be sized and dimensioned to extend into a lumen of an aortic branch vessel.

Unlike the scallop regions 42 and 78 discussed above, the scallop region 102 of the frame structure 100 shown in FIGS. 5A-6B can comprise a continuous, ring-shaped wire 112. The Z-shaped struts 34 comprising the Z-form region 36 can be directly connected to, or extend from, the wire 112. Similarly, the backstop 66 can be directly connected to, or extend from, the wire 112. Integration of the frame structure 100 into a stent graft is described below.

Stent Grafts

Another aspect of the present disclosure can include a stent graft for implantation in a diseased blood vessel, such as a diseased aortic arch 12. The stent graft can be movable between a collapsed configuration and an expanded configuration. The stent graft can comprise an elongated body having a proximal end portion, a distal end portion, an intermediate portion extending between the proximal and distal end portions, and a lumen extending between the proximal and distal end portions. The proximal end portion can include a frame structure, and the intermediate and distal end portions can include an expandable support member. As discussed below, the frame structure can be configured as any one or combination of the frame structures discussed above. Each of the frame structure and the expandable support member can have at least one surface thereof covered by a biocompatible graft material. The proximal end portion can include an aperture that is in fluid communication with the lumen, and is defined by a portion of the frame structure. The frame structure can include a deployable backstop configured to extend into a lumen of an aortic arch branch vessel when the stent graft is implanted in a subject.

One example of a stent graft 114 is shown in FIGS. 1A-B. In this example, the stent graft 114 can have a flexible, tube-like configuration and be adapted for placement in a bodily vessel, such as an aortic arch 12. The stent graft 114 can be configured to engage an inner surface of a bodily vessel so that an elongated body 116 thereof forms a substantial seal with the inner surface of the bodily vessel. The stent graft 114 can be compressed to facilitate delivery to a bodily vessel, and then selectively expanded by, for example, a deployment mechanism 118 (e.g., a balloon, stent, etc.) so that the stent graft substantially conforms to the inner surface of the bodily vessel. As shown in FIG. 1B, the elongated body 116 can include a proximal end portion 120 defining a first opening 122, a distal end portion 124 defining a second opening (not shown), an intermediate portion 126 extending between the proximal and distal end portions, and a lumen 128 extending between the proximal and distal end portions. In some instances, the proximal end portion 120 of the body 116 can include a sewing ring (not shown) attached thereto. The sewing ring can have a circular or oval-like shape and be adapted for suturing to a portion of a bodily vessel, such as a portion of an aortic arch 12. The sewing ring can be securely attached to the body 116 of the stent graft 114 using any one or combination of known attachment means (e.g., staples, clips, sutures, adhesives, etc.). The sewing ring can be comprised of any suitable biocompatible material including, for example, woven polyester, DACRON, TEFLON, PTFE and/or any one or combination of the biocompatible materials disclosed below.

In another aspect, the proximal end portion 120 of the elongated body 116 can include a frame structure 30 or 76. The intermediate portion 126 and the distal end portion 124 of the elongated body 116 can include an expandable support member 130. Each of the frame structure 30 or 76 and the expandable support member 130 can be stitched into graft material 132 comprising the stent graft 114. Each of the frame member 30 or 76 and the expandable support member 130 can have at least one surface thereof covered by the graft material 132 (e.g., a biocompatible graft material). The graft material 132 can include any biocompatible material that is mechanically stable in vivo and is capable of preventing or substantially reducing the possibility of the passage or flow of blood or other body fluids through the stent graft 114. Examples of suitable materials for use in constructing the stent graft 114 can include biocompatible plastics, such as woven polyester, non-resorbable elastomers or polymers such as silicone, SBR, EPDM, butyl, polyisoprene, Nitril, Neoprene, nylon alloys and blends, poly(ethylene-vinyl-acetate) (EVA) copolymers, silicone rubber, polyamides, polyurethane, poly(ester urethanes), poly(ether urethanes), poly(ester urea), polypropylene, polyethylene, polycarbonate, polytetrafluoroethylene (PTFE) (e.g., TEFLON), expanded PTFE (ePTFE), polyethylene terephthalate (e.g., DACRON), and polyethylene copolymers. It will be appreciated that the stent graft 114 can additionally or optionally include a layer of biological material (not shown), such as bovine or equine pericardium, peritoneal tissue, an allograft, a homograft, a patient graft, or a cell-seeded tissue. The layer can cover the entire stent graft 114 or only a portion thereof. One skilled in the art will appreciate that other materials suitable for vascular surgical applications may also be appropriate for the stent graft 114.

In another aspect, the expandable support member 130 can have an inner surface (not shown in detail) that defines a lumen (not shown). In some instances, the expandable support member 130 can have a single, unitary configuration, whereas in other instances, the expandable support member can be comprised of a series of discrete units (e.g., each unit having a Z-stent configuration) (not shown). The structure of the expandable support member 130 may be a mesh, a zigzag wire, diamond-shaped, a spiral wire, an expandable stent, or other similar configuration that allows the expandable support member to be collapsed and expanded. The expandable support member 130 can be comprised of a material having a high modulus of elasticity, including, for example, cobalt-nickel alloys (e.g., Elgiloy), titanium, nickel-titanium alloys (e.g., Nitinol), cobalt-chromium alloys (e.g., Stellite), nickel-cobalt-chromium-molybdenum alloys (e.g., MP35N), graphite, ceramic, stainless steel, and hardened plastics. The expandable support member 130 may also be made of a radio-opaque material or include radio-opaque markers (not shown) to facilitate fluoroscopic visualization. Examples of radio-opaque materials are known in the art and can include, but are not limited to, gold, gallium, technetium, indium, strontium, iodine, barium, bromine and phosphorus-containing compounds. As described in more detail below, radio-opaque markers can be used to facilitate implantation of the stent graft 114 in a bodily vessel.

In another aspect, the stent graft 114 can include an aperture 134 at least partly or entirely defined by the aperture 50 or 84 of the scallop region 42 or 78. For example, the aperture 134 can be located about an upper portion 136 of the proximal end portion 120. The aperture 134 can be sized and dimensioned so that the lumen 128 of the elongated body 116 is in fluid communication with the lumen of each of the aortic arch branch vessels 14 when the stent graft 114 is implanted in a subject. The aperture 134 can have any desired length and width sufficient to promote leak-proof attachment of the aortic arch branch vessels 14 to the elongated body 116. In some instances, the aperture 134 can have an elongated, oval-like shape; however, it will be appreciated that other shapes are possible.

In another aspect, and as discussed above, the backstop 66 can be self-expanding and thereby automatically deploy during expansion of the stent graft 114. In other instances, a deployment mechanism (not shown) (e.g., a pullwire) may be used to selectively deploy the backstop 66. As shown in FIGS. 6A-B, for instance, the backstop 66 can have a longitudinal axis $LA_s$. When the stent graft 114 is in the collapsed configuration, the backstop 66 can be positioned such that the longitudinal axis $LA_s$ is parallel to, or substantially parallel to, a longitudinal axis $LA_m$ of the elongated body 116 (FIG. 6A). In the expanded configuration, the longitudinal axis $LA_s$ of the backstop 66 can be tangential (e.g., orthogonal) to the longitudinal axis $LA_m$ of the elongated body 116 (FIG. 6B). The backstop 66 can be automatically or manually deployed. To provide for automatic deployment, the elongated body 116 of the stent graft 114 can include a detachable strip 138 (FIG. 1A). The detachable strip 138 can include a section of material that overlies the aperture 134 and the backstop 66 when the elongated body 116 is in the collapsed configuration. The detachable strip 138 can be made of the same or a different material as the graft material 132 of the stent graft 114, so long as the detachable strip can be easily removed (e.g., by tactile force). Thus, in some instances, the detachable strip 138 can have a perimeter defined by a series of perforations (not shown) that permit easy removal of the detachable strip from stent graft 114. As described in more detail below, the detachable strip 138 can be peeled away from the elongated body 116 (e.g., in a distal-to-proximal direction). Upon doing so, the backstop 66 can automatically "pop-up" and obtain a deployed configuration whereby the longitudinal axis $LA_s$ of the backstop 66 is tangential to the longitudinal axis $LA_m$ of the elongated body 116. The detachable strip 138 can be further peeled away from the elongated body 116 to expose the aperture 134.

Another example of a stent graft 140 according to the present disclosure is illustrated in FIGS. 5A-C. The stent graft 140 can be identically constructed as the stent graft 114 shown in FIGS. 1A-B, except where described below. Thus, structures with the same reference numbers in FIGS. 1A-B are identical to the structures with the same reference number in FIGS. 5A-C, whereas different structures use different reference numbers. The stent graft 140 can be movable between a collapsed configuration and an expanded configuration. The stent graft 140 can comprise an elongated body 142 having a proximal end portion 144, a distal end portion 124, an intermediate portion 126 extending between the proximal and distal end portions, and a lumen 146 extending between the proximal and distal end portions. The proximal end portion 144 can include a frame structure 100, and the intermediate portion 126 and the distal end portion 124 can include an expandable support member 130. Each of the frame structure 100 and the expandable support member 130 can have at least one surface thereof covered by a biocompatible graft material 132. The proximal end portion 144 can include an aperture 148 that is in fluid communication with the lumen 146, and is defined by a portion of the frame structure 100. The frame structure 100 can include a deployable backstop 66 configured to extend into a lumen of an aortic arch branch vessel when the stent graft 140 is implanted in a subject.

Unlike the stent graft 114 in FIGS. 1A-B, the proximal end portion 144 of the stent graft 140 can have a basket-like configuration (e.g., by virtue of the frame structure construction) when the elongated body 142 is in the expanded configuration. The cross-sectional profile of the proximal end portion 144 can be asymmetrical. As shown in FIG. 5B, for example, an upper portion 150 of the proximal end portion 144 can have a width W1 that is greater than the width W2 of a lower portion 152 of the proximal end portion. The asymmetric cross-sectional profile can promote optimal seal formation between the greater and lesser curves of the aortic arch 12 and the upper and lower portions 150 and 152, respectively, of the proximal end portion 144. Consequently, the shape of the proximal end portion 144 promotes movement of blood through the stent graft 140 while maintaining patency of the lumen 146. The structure of the proximal end portion 144 may be the same or different than the structure of the rest of the elongated body 142. To accommodate the basket-shape configuration of the proximal end portion 144, for example, the frame structure 100 of the proximal end portion can include Z-shaped struts 34 oriented in the opposite direction from the rest of the expandable support member 130, a coil-like configuration, or some other self-expanding weave.

Methods

Another aspect of the present disclosure can include a method 154 for repairing a diseased blood vessel in a subject, such as an aneurysm of the aortic arch 12. The method 154 can include the steps of: providing a stent graft (Step 156); positioning the stent graft in a diseased aortic arch of a subject so that a backstop thereof is located immediately adjacent the aortic arch branch vessels (Step 158); deploying the backstop (Step 160); and securely implanting the stent graft in the subject (Step 162). In some instances, the method 154 can be used to treat DeBakey type I acute aortic dissections. For example, the method 154 can be adapted based on the procedure of Roselli et al., *J Thorac Cardiovasc Surg.*, 145(3 Suppl):S197-201 (March 2013). The method 154 can also be used for repair of thoracic aorta disease in both ascending arch and descending thoracic aorta (Svensson et al., *Ann Thorac Surg.*, 96:548-58 (2013).

To repair an aortic arch aneurysm, for example, an open-chest frozen elephant trunk procedure using the stent graft 114 shown in FIGS. 1A-B can be employed. Although implantation of the stent graft 114 is described below using an open surgical approach, it will be appreciated that other methods for implanting the stent graft, such as a percutaneous or minimally invasive surgical technique may be used, as well as other configurations of the stent graft described herein.

Figure 8:
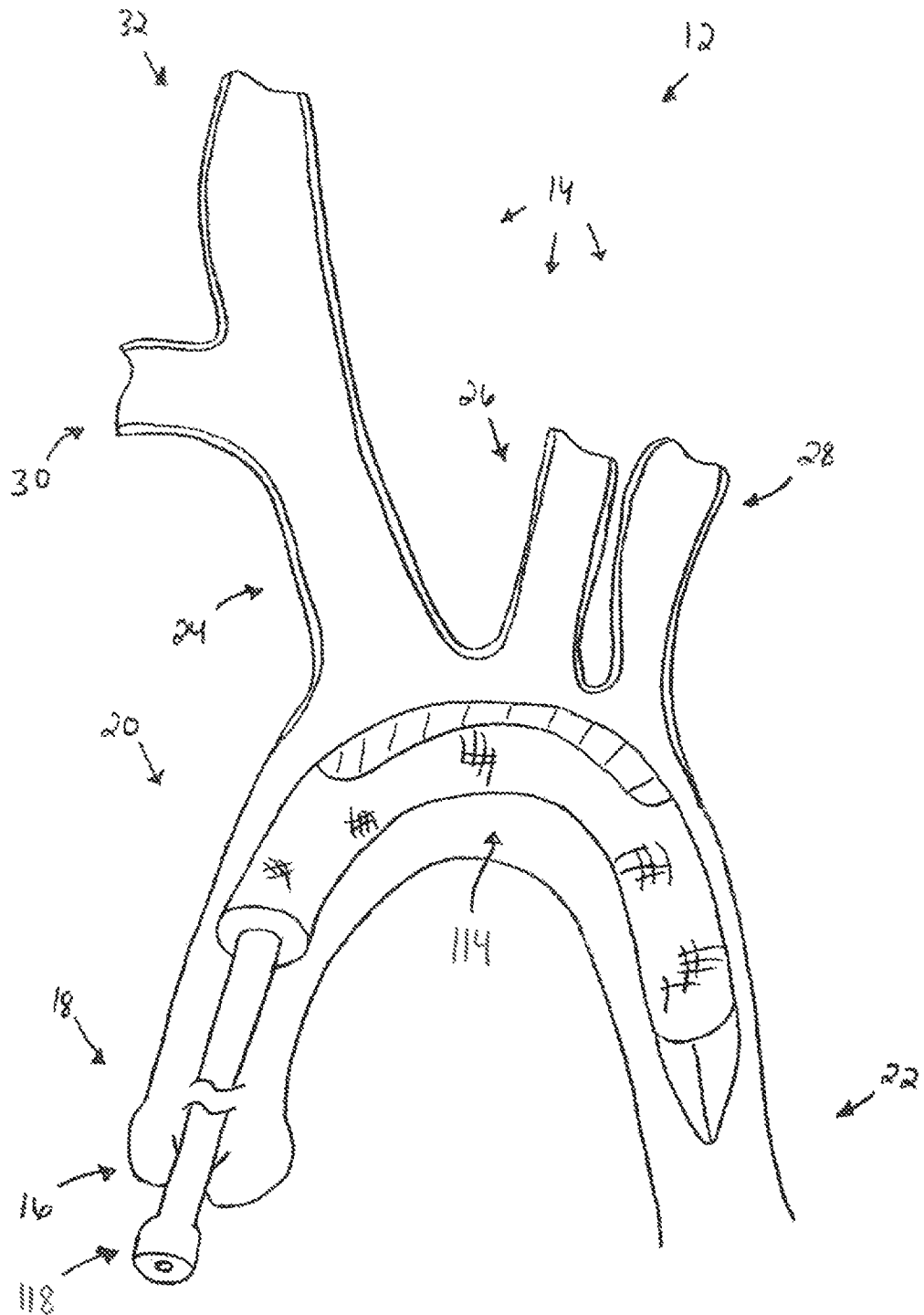
FIG. 8 is a perspective view showing the stent graft in FIG. 1A being inserted into a diseased aortic arch.
Figure 9:
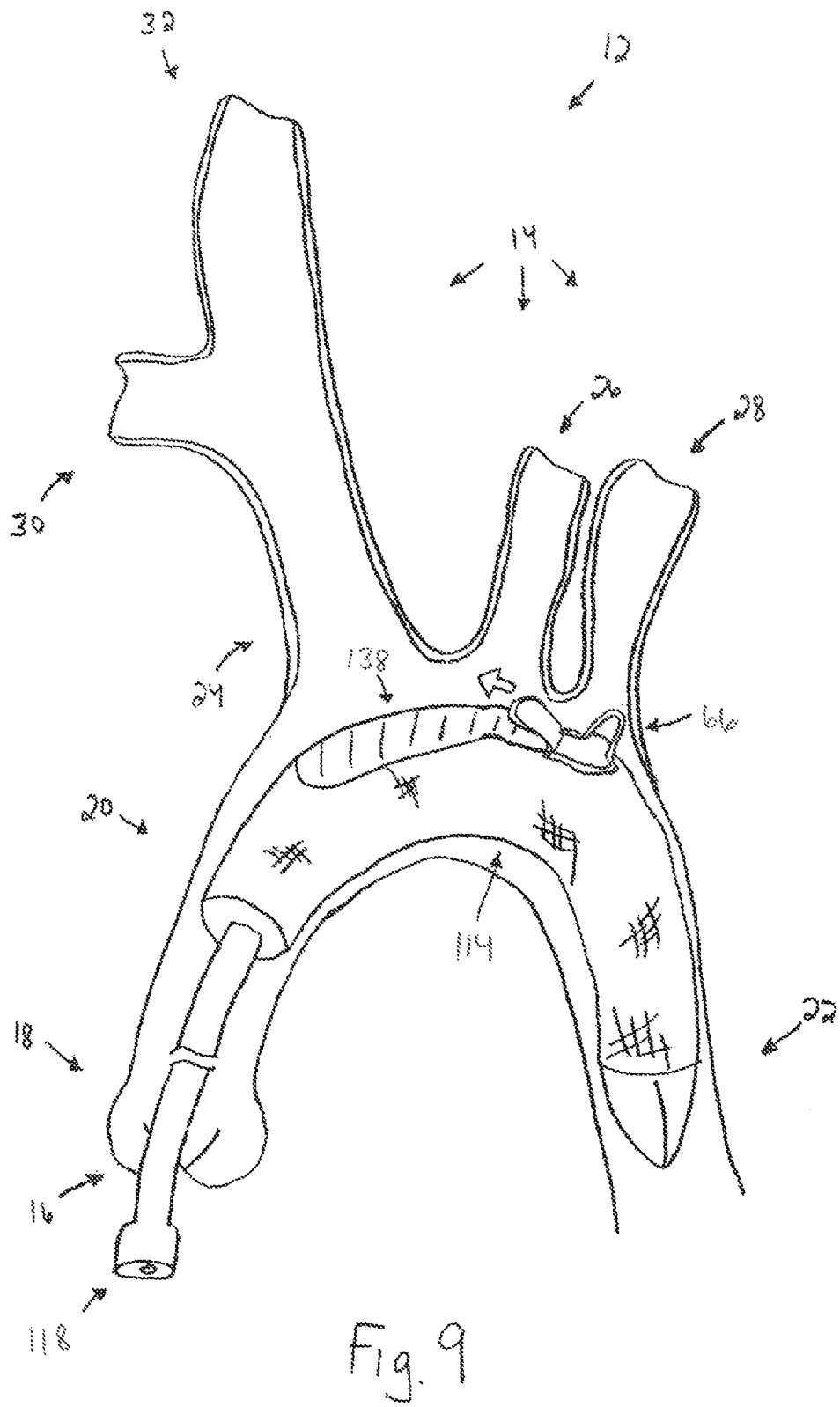
FIG. 9 is a perspective view showing the backstop of the stent graft in FIG. 8 being deployed into a left subclavian artery.

After providing a stent graft 114 at Step 156, a placement position for the stent graft in the aortic arch 12 can be determined using a known imaging technique, such as fluoroscopy, angiography, ultrasonography, CT, helical CT, CT angiogram, MRI, and/or MR angiography. Prior to implanting the stent graft 114, the stent graft can be loaded onto a delivery mechanism 118 to facilitate delivery of the stent graft to the aortic arch 12 in the collapsed configuration. After loading the stent graft 114 onto the delivery mechanism 118, the delivery mechanism can be inserted into the aortic arch 12 via an incision (not shown). As shown in FIG. 8, the delivery mechanism 18 can be positioned in the aortic arch 12 so that a detachable strip 138 is positioned immediately or directly adjacent the aortic arch branch vessels 14 (Step 158). Once the delivery mechanism 118 and the stent graft 114 are appropriately positioned in the aortic arch 14, the detachable strip 138 can be peeled away from the elongated body 116 in a distal-to-proximal direction (Step 160). As the detachable strip 138 is progressively peeled away (indicated by arrow in FIG. 9), the backstop 66 automatically "pops-up" and obtains the deployed erect configuration. In the erect configuration, all or only a portion of the backstop 66 extends into the lumen of an aortic arch branch vessel 14, such as the left subclavian artery 28. In some instances, at least a portion of the backstop 66 can be in physical contact with a portion of the left subclavian artery 28, such as the origin of the left subclavian artery. The detachable strip 138 can then be further peeled away from the elongated body 116 to expose the aperture 134.

Figure 10:
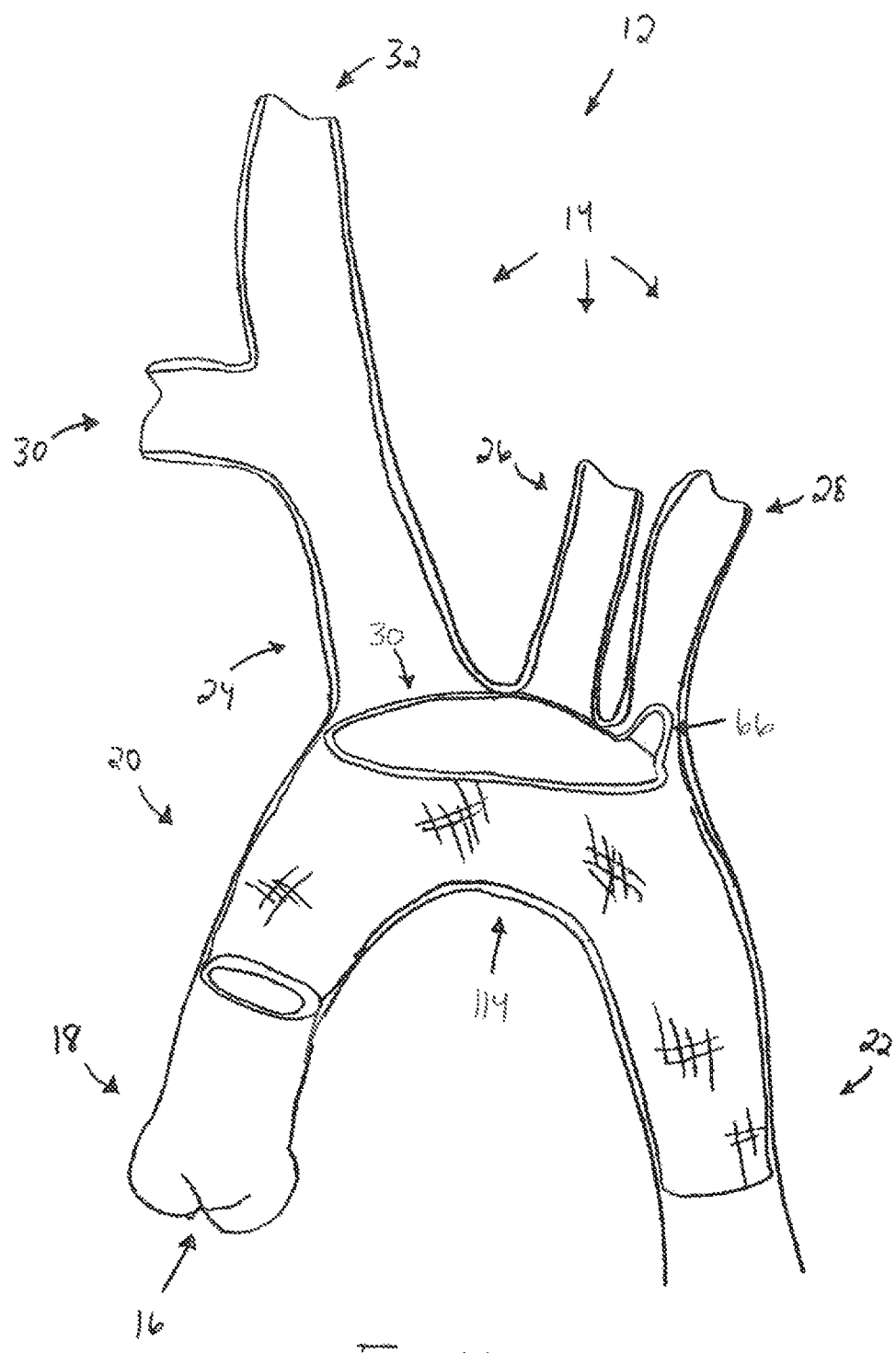
FIG. 10 is a perspective view showing the stent graft in FIG. 1B securely implanted in the diseased aortic arch.

After the detachable strip 138 has been completely removed from the stent graft 114, the rest of the elongated body 116 can be expanded as shown in FIG. 10. In the expanded configuration, the lumen of each of the aortic arch branch vessels 14 can be in fluid communication with the lumen 128 of the stent graft 114. Thereafter, the incision in the aortic arch 12 can be closed and the vessels surrounding the stent graft 114 unclamped so that blood can flow normally through the stent graft. Conventional stent grafts, once implanted, often suffer from migration due to pulsatile blood flow, non-optimal construction, etc. Advantageously, the backstop 66 can prevent migration of the stent graft 114 once implanted by resisting the flow of blood through the aorta. It will be appreciated that expansion and implantation of the stent graft 114 may be varied as needed. In some instances, for example, the backstop 66 can be constrained until the entire elongated body 116 is expanded. In other instances, a portion of the stent graft 114 (e.g., the proximal end portion 120) may first be expanded, advanced into the aorta, and then the remainder of the stent graft expanded.

From the above description of the present disclosure, those skilled in the art will perceive improvements, changes and modifications. For example, it will be appreciated that the order of steps described above for implanting the stent graft 114 are intended to be illustrative only and are not intended to limit the present disclosure to the order of steps described herein. Such improvements, changes, and modifications are within the skill of the art and are intended to be covered by the appended claims. All patents, patent applications, and publications cited herein are incorporated by reference in their entirety.

The following is claimed:

1. A frame structure adapted for use with a stent graft, the frame structure comprising:
    a scallop region having a first end portion, a second end portion, and a perimeter that defines an aperture; and
    a Z-form region extending from the scallop region and comprising a plurality of Z-shaped struts, each of which has a first end and a second end that is connected to the scallop region at different points so as to form a central frame structure lumen, wherein the scallop region includes a plurality of attachment members spaced apart from one another by one or more peak-shaped structures;
    wherein the second end portion of the scallop region includes a backstop that is deployable from a first flattened configuration to a second erect configuration;
    wherein the backstop, in the second erect configuration, is sized and dimensioned to extend into a lumen of an aortic branch vessel.

2. The frame structure of claim 1, having an arch-shaped centerline that mirrors the arch-shaped centerline of an aortic arch.

3. The frame structure of claim 1, wherein each of the attachment members is omega-shaped and includes an arcuate portion that is free from direct attachment to any of the Z-shaped struts.

4. The frame structure of claim 1, wherein each of the peak-shaped structures includes an apex that is connected to the first or second of one of the Z-shaped struts.

5. The frame structure of claim 1, wherein each of the attachment members is peak-shaped.

6. The frame structure of claim 1, wherein each of the peak-shaped attachment members is spaced apart from one another by first and second peak-shaped structures, each of the first and second peak-shaped structures having an apex that is free from direct attachment to any of the Z-shaped struts.

7. A stent graft that is movable between a collapsed configuration and an expanded configuration, the stent graft comprising:
    an elongated body having a proximal end portion, a distal end portion, an intermediate portion extending between the proximal and distal end portions, and a lumen extending between the proximal and distal end portions, the proximal end portion including a frame structure and the intermediate and distal end portions including an expandable support member, each of the frame structure and the expandable support member having at least one surface thereof covered by a biocompatible graft material;
    wherein the proximal end portion includes an aperture that is in fluid communication with the lumen and defined by a portion of the frame structure, the frame structure including a deployable backstop configured to extend into a lumen of an aortic arch branch vessel when the stent graft is implanted in a subject;
    wherein the backstop extends radially away from the main body when the stent graft obtains the expanded configuration.

8. The stent graft of claim 7, wherein the covering further includes a detachable strip that overlies the aperture and the backstop when the stent graft is in the collapsed configuration.

9. The stent graft of claim 8, wherein the backstop is automatically deployed upon removal of the detachable strip from over the backstop.

10. The stent graft of claim 7, wherein the aperture is sized and dimensioned so that the lumen of the main body is in fluid communication with the lumen of each of the aortic arch branch vessels when the stent graft is implanted in a subject.

11. The stent graft of claim 7, wherein the stent frame further comprises:
    a scallop region having a first end portion, a second end portion, and a perimeter that defines an aperture; and
    a Z-form region extending from the scallop region and comprising a plurality of Z-shaped struts, each of which has a first end and a second end that is connected to the scallop region at different points so as to form a central frame structure lumen;

wherein the second end portion of the scallop region includes the backstop.

12. The stent graft of claim 11, wherein the frame structure has an arch-shaped centerline that mirrors the arch-shaped centerline of an aortic arch.

13. A stent graft that is movable between a collapsed configuration and an expanded configuration, the stent graft comprising:

an elongated body having a proximal end portion, a distal end portion, an intermediate portion extending between the proximal and distal end portions, and a lumen extending between the proximal and distal end portions, the proximal end portion including a frame structure and the intermediate and distal end portions including an expandable support member, each of the frame structure and the expandable support member having at least one surface thereof covered by a biocompatible graft material;

wherein the proximal end portion includes an aperture that is in fluid communication with the lumen and defined by a portion of the frame structure, the frame structure including a deployable backstop configured to extend into a lumen of an aortic arch branch vessel when the stent graft is implanted in a subject;

wherein the aperture is sized and dimensioned so that the lumen of the main body is in fluid communication with the lumen of each of the aortic arch branch vessels when the stent graft is implanted in a subject;

wherein the aperture is sized and dimensioned so that the lumen of the main body is in fluid communication with the lumen of each of the aortic arch branch vessels when the stent graft is implanted in a subject.

* * * * *